Figure 1:
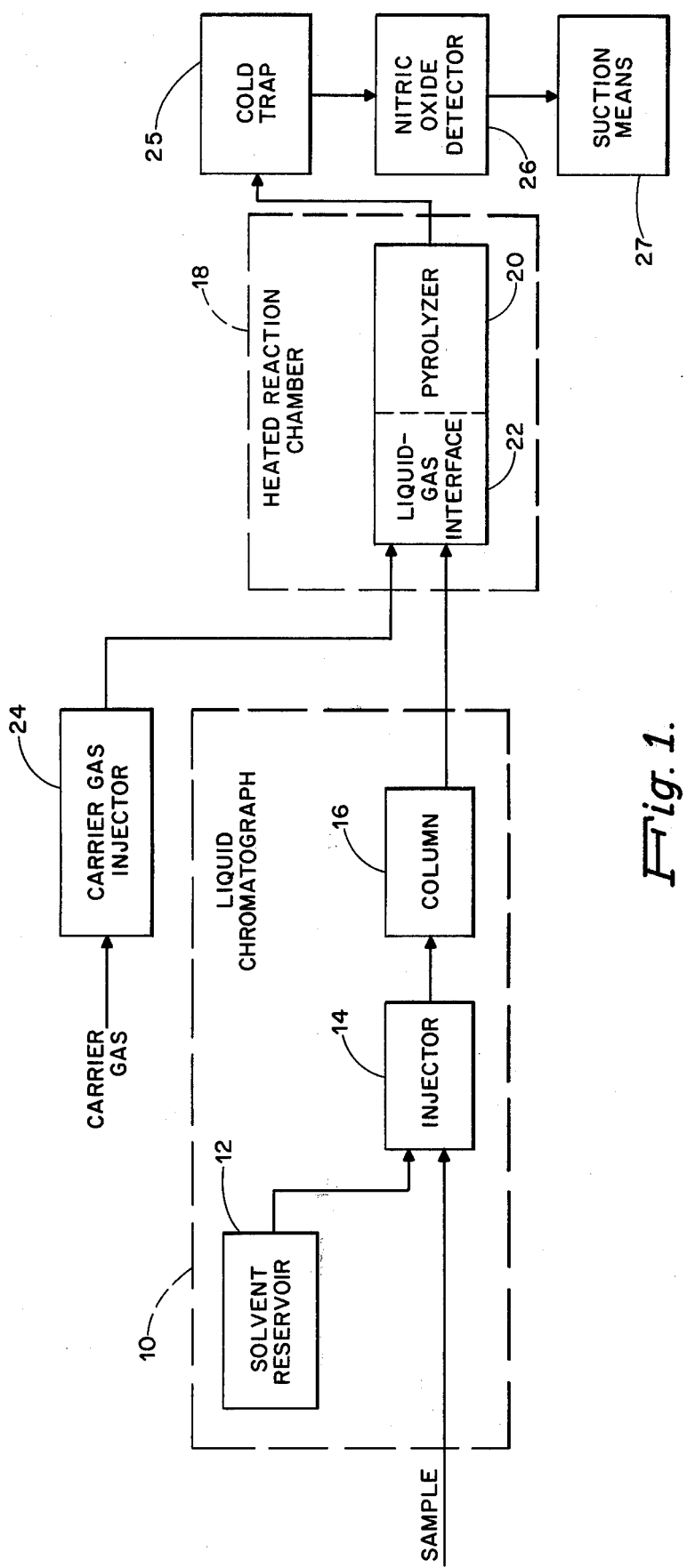
Figure 2:
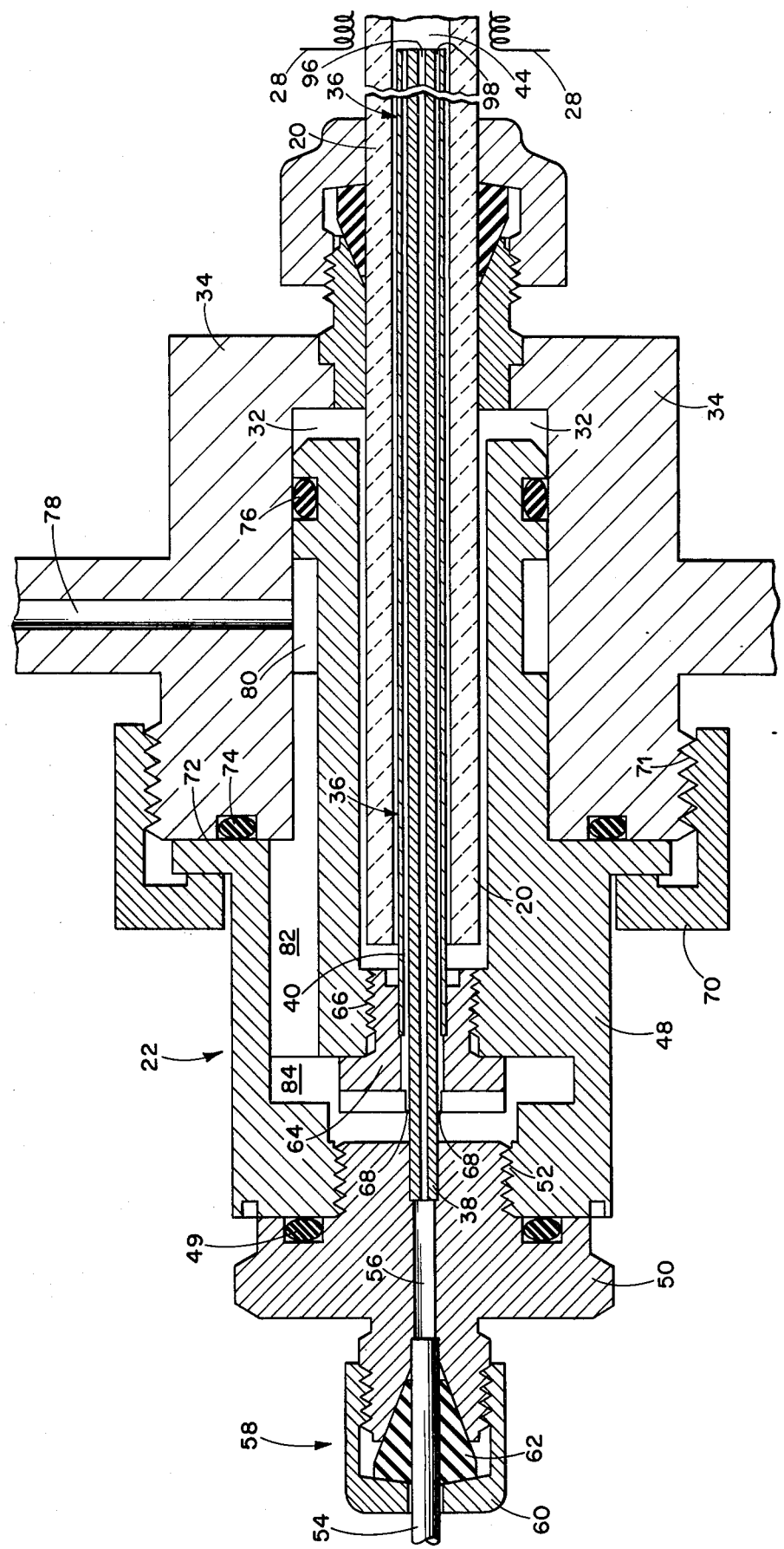

United States Patent [19]

Fine et al.

[11] 4,066,411
[45] Jan. 3, 1978

[54] N-NITROSO COMPOUND ANALYZER WITH SAMPLE ATOMIZATION

[75] Inventors: David H. Fine, Framingham; John J. Fronduto, Waltham; David P. Rounbehler, Harwichport, all of Mass.

[73] Assignee: Thermo Electron Corporation, Waltham, Mass.

[21] Appl. No.: 760,603

[22] Filed: Jan. 19, 1977

[51] Int. Cl.² ............................................. G01N 31/08
[52] U.S. Cl. ........................... 23/253 PC; 23/230 PC; 23/254 R; 73/61.1 C
[58] Field of Search ........ 23/230 PC, 253 PC, 232 R, 23/254 R, 254 E, 255; 73/23.1, 61.1 C; 55/67, 386; 210/24 C, 31 C

[56] References Cited

U.S. PATENT DOCUMENTS

| 3,630,681 | 12/1971 | Arikawa | 210/24 C |
| 3,877,875 | 4/1975 | Jones et al. | 23/230 PC |
| 3,996,003 | 12/1976 | Fine et al. | 23/253 PC |
| 3,996,004 | 12/1976 | Fine et al. | 23/253 PC |

*Primary Examiner*—R.E. Serwin
*Attorney, Agent, or Firm*—James L. Neal; David W. Gomes

[57] ABSTRACT

A liquid-gas interface is provided between a heated reaction chamber of an N-nitroso compound detection system and a liquid chromatograph. The liquid-gas interface atomizes liquid chromatograph effluent, including the N-nitroso compounds to be measured, with a stream of carrier gas, into the reaction chamber. In the heated reaction chamber, the effluent from the interface is vaporized. Condensation of non-volatile N-nitroso compounds is avoided by preheating the liquid effluent prior to atomization.

7 Claims, 2 Drawing Figures

N-NITROSO COMPOUND ANALYZER WITH SAMPLE ATOMIZATION

The invention described herein was made in the course of or under a contract with the U.S. Department of Health, Education and Welfare.

CROSS REFERENCE TO RELATED PATENTS

Subject matter of this application is related to that of U.S. Pat. Nos. 3,973,910, 3,996,002, 3,996,003, 3,996,004, 3,996,008 and 3,996,009.

BACKGROUND OF THE INVENTION

In N-nitroso compound detection systems incorporating liquid chromatography and specific gas detection techniques, the liquid chromatorgraph produces an effluent in which various N-nitroso compounds are separated from each other and from other compounds in a sample in their time of exit from the chromatograph. If this temporal separation is impaired, the accuracy of measurement is adversely affected. Difficulty in efficient liquid-gas conversion may occur particularly with respect to non-volatile N-nitroso compounds which tend to vaporize unevenly or form deposits at the intended conversion point.

N-nitroso compounds are among the most carcinogenic compounds presently known. A single part per million dose may suffice to produce tumors. These compounds have been found in trace quantities in many materials which are contacted or taken internally by humans, such as artificial food additives, tobacco smoke and pesticides. In addition, they may be formed in vivo by taking internally the chemical precursors. In the continuing research into tumor producing substances, N-nitroso compounds require study and there is a need for tolerable levels of human consumption to be determined.

Considerable success has been achieved in the detection and measurement of N-nitroso compounds with systems such as that described in the U.S. patents cross referenced above. However, many such compounds are substantially non-volatile, are difficult to vaporize and are correspondingly difficult to measure with the same level of accurcy achieved with volatile compounds.

Accordingly, it is an object of the present invention to provide a liquid-gas interface capable of efficiently vaporizing non-volatile N-nitroso compounds to increase the accuracy achievable with N-nitroso compound detection systems.

It is a further object of the present invention to provide a liquid-gas interface between a liquid chromatograph and an N-nitroso compound detector which is capable of maintaining a timewise distribution of liquid chromatograph effluent.

SUMMARY OF THE INVENTION

A liquid-gas interface for an N-nitroso compound measurement apparatus is provided. N-nitroso compounds have the general formula:

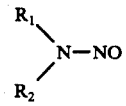

wherein $R_1$ and $R_2$ are the same or differnent organic radicals, including those radicals which together with the non-nitroso N of the above depicted N–NO bond constitute a nitrogen heterocyclic radical. The N–NO bond, the weakest molecular bond, is selectively broken to release nitric oxide in the gaseous phase and then the quantity of liberated nitric oxide is measured. The quantity of nitric oxide released is directly related to the quantity of N-nitroso compounds present. Therefore, measurement of nitric oxide provides an immediate, accurate and direct reading of the N-nitroso compound content of the sample.

In the present apparatus, the N—NO bond is broken by adding an amount of thermal energy to the N-nitroso compound molecules in the sample which is just sufficient to break the N—NO bond, but is insufficient to break bonds in other molecules. The N—NO bond in N-nitroso compounds is typically characterized by a bond strength in the range of 5–12 kcal/mole. In some cases, the bond strength may be as high as 40 kcal/mole, but even this is nearly half the value associated with most other bonds. The energization of the N-nitroso compound molecule liberates nitric oxide according to the following reaction:

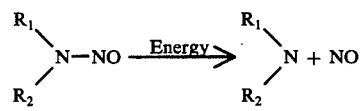

This reaction is accomplished by the non-catalytic pyrolization of the N-nitroso compound molecules in the temperature range 300° C to 500° C. The liberated nitric oxide (NO) may be measured directly or it may be oxidized to form nitrogen dioxide and the amount of nitrogen dioxide measured by conventional techniques.

The measurement apparatus comprises a high performance liquid chromatograph (HPLC) in combination with a pyrolyzer, a cold trap, and a nitric oxide detection means. It will be understood that the HPLC utilizes so-called high performance liquid chromatography, associated with a liquid solvent and a pump, where injection into the column takes place in the liquid phase.

Liquid chromatograph effluent is unjected and atomized into a heated reaction chamber, in this case a pyrolyzer. The pyrolyzer adds thermal energy effective to break the N—NO bond in the N-nitroso compounds present. A cold trap receives the gaseous output of the pyrolyzer and eliminates trace contaminants which might otherwise react in the nitric oxide detector, thereby reducing the margin of error. The nitric oxide detector then measures the nitric oxide present in the gas.

A timewise separation of N-nitroso compounds is maintained from initial input to final output. After pyrolyzation and release of the NO radical, various N-nitroso compounds in the sample are represented by specific readings of nitric oxide at different points in time.

The timewise separation of constituents is maintained through the liquid-to-gas conversion by a nozzle configuration forming the input from the HPLC to the pyrolyzer. The nozzle, or liquid-gas interface, is elongated and extends into the pyrolyzer. A conduit conveys liquid effluent from the chromatograph to the nozzle from which it is injected into the pyrolyzer. A separate passage conveys a stream of inert carrier gas into the pyrolyzer. The liquid effluent and carrier gas absorb heat from the pyrolyzer as it transits the elongated nozzle, thereby raising the temperature of the effluent and the carrier gas, prior to atomization. The liquid effluent is atomized as it is ejected from the nozzle with the carrier gas into the reaction chamber. Heat from the pyrolyzer completes the desired vaporization. A suction device may be employed to draw gasses through the system and to aid atomization in the pyrolyzer.

BRIEF DESCRIPTION OF THE DRAWINGS

FIG. 1 is a block diagram of a measuring system incorporating the present invention.

FIG. 2 is a sectional view of a liquid-gas interface embodying the present invention.

DETAILED DESCRIPTION OF THE DRAWINGS

In FIG. 1, a N-nitroso compound measurement system is shown. A liquid chromatograph 10 includes a solvent reservoir 12, an injector 14 and a chromatograph column 16. A heated reaction chamber 18 for receiving liquid chromatograph effluent includes a gas interface 22 and a pyrolyzer 20. A carrier gas injector 24 provides carrier gas to the liquid-gas interface 22. A cold trap 25 receives gaseous output from the pyrolyzer 20 and filters various interfering substances from that output. A nitric oxide detector 26 receives the filtered gases from the cold trap 25 and measures the amount of nitric oxide present in the sample. Suction means 27 at the output of the gas detector 26 helps to draw the effluent and carrier gas from the interface 22, through the pyrolyzer 20, through the cold trap 25 and into the nitric oxide detector 26. A system similar to that of FIG. 1, depicting a liquid chromatograph and specific gas detector combination, is described in greater detail in the above-noted U.S. Pat. No. 3,996,003.

The injector 14 includes a pump for forcing the solvent and sample through the column in the liquid phase. The separation can be liquid-liquid, or liquid-solid, e.g. liquids filtering through a packed dry bed. In such high performance liquid chromatography, the solvent and the sample to be separated by the chromatogrph are force-fed into and through the chromatograph, thus causing the output of the chromatograph to be under a certain pressurization. The pressure of the chromatograph effluent may be varied according to the resistance afforded the solvent by the chromatograph packing to maintain flow through the chromatograph constant.

The chromatograph pressure feeds the liquid effluent into the pyrolyzer 20 through a restricted passageway in the liquid-gas interface 22. While it is in the liquid-gas interface 22 the liquid effluent absorbs heat from the heated reaction chamber 18 and is atomized. As the effluent is atomized into the pyrolyzer 20, it is mixed with carrier gas supplied by the carrier gas injector 24, the carrier gas also having been heated by the heated reaction chamber prior to mixing. The carrier gas helps to carry the gaseous constituents through the pyrolyzer 20, the cold trap 25 and into the nitric oxide detector 26. The essential criteria for selection of a carrier gas is that it be inert in the pyrolyzer 20 and the detector 26. Examples of such gas are argon, helium and nitrogen.

Once vaporized within the pyrolyzer the N-nitroso compounds undergo chemical changes. The pyrolyzer adds the amount of thermal energy effective to liberate the NO radical from the structure of the various N-nitroso compound molecules without breaking other molecular bonds therein. This selective liberation of the NO radical may occur by maintaining the temperature of the pyrolyzer between 300° and 500° C. Further details appear in the above-referenced U.S. patents.

The cold trap 25 receives the gaseous output of the pyrolyzer 20 and filters it to substantially eliminate trace contaminants which might otherwise cause interference in the NO detector and increase the margin of error.

The gaseous output of the cold trap 25 is received by the nitric oxide detector 26. The nitric oxide detector may be a chemiluminescent type having a chemiluminescent reaction chamber and a photo-sensitive device for sensing the reaction, neither of which are shown. Specifically, in such a nitric oxide detector, nitric oxide in the test gases comes into the presence of ozone and a chemiluminescent reaction results. The photosensitive device senses the intensity of the chemiluminescent reaction and provides a signal proportional thereto. The intensity of the reaction is a function of the quantity of nitric oxide present. A nitric oxide detector which may be used in the present measurement system is the Model 502 NO—$NO_x$ analyzer manufactured by Thermo Electron Corporation of Waltham, Mass.

As mentioned, the suction means 27 is connected to the output of the nitric oxide detector 26 to aid the flow of gases from the liquid-gas interface 22 through the measurement system to the nitric oxide detector 26. A vacuum means capable of supplying a pressure between 1 - 10 torr is suitable for the present measuring system. The vacuum created by the suction means 27 appears in the system from the liquid gas interface 22 through the nitric oxide detector 26. Thusly, it aids in the atomization and vaporization of liquid chromatograph effluent at the interface 22 as well as helping to draw those gases and the products of pyrolyzation through the pyrolyzer 20, through the cold trap 25 and through the nitric oxide detector 26.

FIG. 2 shows one embodiment of the liquid gas interface 22 of the present invention extending into a ceramic tube 44 forming the reaction chamber 18. The ceramic tube is heated from without by an electric heating means 28, the heating means and a portion of the ceramic tube downstream from the interface forming the pyrolyzer 20.

The interface 22 is mounted within a cavity 32 in the housing 34 so that it extends into the ceramic tube, one end of the tube being appropriately mounted within the housing 34. The interface 22 includes a nozzle means 36 formed by an inner cylindrical tube 38 for liquid chromatograph effluent and a concentrically arranged outer cylindrical tube 40 for carrier gas. The nozzle means 36 discharges the liquid effluent mainly under the pressure resulting from the high performance chromatograph, and mixes the effluent with carrier gas, also discharged from the nozzle means 36, to atomize the effluent.

The interface structure 22 is supported by housing members 48 and 50 which are interconnected at a threaded portion 52. An annular sealing means 49 between the members 48 and 50 forms a gas-tight seal. An input conduit 54 from the liquid chromatograph is attached to housing member 50 and is in fluid communication with a bore 56 through the interior of member 50. In the present embodiment, a compression fitting 58 comprising a ring 60 and a ferrule 62 is used for the connection of the input conduit 54; however, any suitable connection means would suffice. The other end of the bore 56 connects with the inner cylindrical tube 38, which tube receives structural support from the housing member 50.

The interface housing member 48 has an internal bore, part of which serves as a mount for a tube holding member 64. The members 64 and 48 are interconnected along a threaded portion 66. The member 64 is attached to and serves as structural support for the outer cylindrical tube 40, the member 64 having an internal bore 68 therethrough which is in fluid communication with the outer cylindrical tube. The diameters of the bore 68 and the inside of the outer cylindrical tube 40 are both larger than the outer diameter of the inner cylindrical tube 38 to allow carrier gas to pass through an annular passageway in the tube 40, around the inner cylindrical tube 38. In one embodiment of the present invention, the outer diameter of the outer cylindrical tube 40 is 0.100 inches (0.254 cm). The pyrolyzer chamber that this particular delivery means was designed for is a ceramic tube with a 0.125 inch (0.3165 cm) inner diameter and a 0.250 inch (0.633 cm) outer diameter.

The interface housing member 48 is designed for removable connection with the housing 34. A coupling ring 40, in threaded engagement 71 with the housing 34, exerts pressure on the interface housing member 48 to cause contact with the housing 34 along the annular surface 72. An annular sealing means 74 located along the surface 72 provides a gas-tight seal between the housing member 48 and the housing 34. Another annular sealing means 76 is located in an annular cavity around the end of the housing member 48 to form a gas-tight seal between the housing member 48 and the housing 34.

A carrier gas conduit 78 passes through the housing 34 into a cavity or annular channel 80 formed within the housing member 48. A groove 82 extends from the cavity 80 and establishes fluid communication with a cavity 84 between housing members 48 and 50. The cavity 84 is in fluid communication with the bore 68 of the member 64.

Normally the liquid chromatograph effluent retains sufficient pressurization from its injection input to propel it through the interface of the present invention. Therefore, the input conduit 54 is connected directly from the liquid chromatograph. The effluent is conveyed through the inner cylindrical tube 38 into the reaction chamber 44, through the port 96. Carrier gas enters the interface under pressure above that in the reaction chamber 44 and passes through the conduit 78, into the cavity 80, through the groove 82, and into the cavity 84. It then passes through the annular opening 68, through the bore in member 64 and the outer conduit 40 where it exits through the port 98. The carrier gas may be propelled by a source of compressed gas feeding the conduit 78 or by a vacuum pump associated with the specific gas detector 26. Upon discharge from the port 98, the carrier gas assists in atomizing liquid effluent from the port 96.

Prior to atomization both the liquid effluent and the carrier gas are heated during passage through the elongated nozzle means 36. The temperature attained in the nozzle means 36, for a given reaction chamber temperature, is determined by the extent to which the nozzle means 36 extends inside the reaction chamber 44. After discharge of effluent from the nozzle means 36, atomized effluent is propelled through the reaction chamber 44 by the carrier gas. Heat from the reaction chamber completes vaporization and pyrolyzes or otherwise produces the desired reaction in the effluent.

The position of dischargeend of the nozzle means 36 within the reaction chamber 44 is selected to determine its operating temperature. If the nozzle means 36 and its contents are not preheated, non-volatile compounds may be frozen during atomization. This effect tends to be more prominent when non-volatile compounds are carried in a solvent having a low boiling point and a high vaporization pressure (e.g., dichlorolmethane, ether and pentane). Adiabatic expansion of such carrier solvents absorbs heat and causes the freezing and condensation of the non-volatile substances. On the other hand, if the nozzle means 36 is allowed to reach too high a temperature, the solvent may vaporize prematurely and deposits of the non-volatile specific compounds will be formed and result in either irregular vaporization or clogging of the port 96. Therefore, the nozzle oosition is determined so that the effective temperature of the effluent upon discharge is sufficiently high that adiabatic expansion of liquid chromatograph solvents will not lower the temperature of the non-volatile constituents to a level where freezing thereof will occur. On the other hand, the temperature must be below the level which will cause premature vaporization of the solvents (e.g., evaporation of the solvents while in tube 40) and tend to produce deposits of the non-volatile constituents in the nozzle means 36.

The position of the nozzle means 36 and its corresponding operating temperature are predetermined according to various operating parameters. Major parameters which affect the operating temperature of the end of the nozzle means 36 are the temperature of the reaction chamber 44, the initial temperature of the liquid effluent and the carrier gas, the particular solvents and carrier gas being used, and the flow rate of the liquid effluent and the carrier gas.

In one embodiment of the present invention, the reaction chamber 44 is formed by a ceramic tube approximately 22 inches long heated by an external electric heating element 28 beginning a short distance from the housing 34 and extending approximately to the downstream end of the ceramic tube. With an exterior operating temperature of 550° C for the ceramic tube, an interior temperature of between 400° and 500° C can be achieved. In this temperature range, if the position of the discharge end of the nozzle means 36 is approximately 0.75 inches upstream from the beginning of the heating element 28, its operating temperature can approximate 100° C, depending upon flow rate and other factors. Similarly, if the nozzle discharge end coincides with the position of the leading edge of the heating element 28, a nozzle tip operating temperature of approximately 500° C can be attained. It will be understood that, other conditions being the same, intermediate positions will produce intermediate temperatures. In one embodiment, satisfactory results have been achieved by positioning the end of the nozzle means 36 between 0.25 and 0.50 inches (0.635 to 1.27 cm) from the leading edge of the heating element 28.

As various changes could be made in the above constructions without departing from the scope of the invention, it should be understood that all matter contained in the above description or shown in the accompanying drawings shall be interpreted as illustrative and not in a limiting sense.

We claim:

1. Apparatus for measuring in a sample the amount of N-nitroso compounds having the general formula:

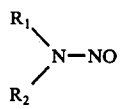

wherein $R_1$ and $R_2$ are the same or different organic radicals, including those radicals which together with the non-nitroso N of the depicted N—NO bond constitute a nitrogen heterocyclic radical, and wherein the N—NO bond is the weakest bond in the molecule, comprising:

A. high performance chromatograph including a column, having an input end for receiving said sample in liquid solution form with a solvent and an output end for ejecting column effluent, wherein the ejection of the N-nitroso portion having N-nitroso compounds therein is separate in time from the ejection of other portions of said sample having other compounds therein and further wherein ejections of portions having different N-nitroso compounds are separate in time from each other;

B. chamber means for pyrolyzing said column effluent at a temperature in the range 300° to 500° C to liberate from said N-nitroso compounds nitric oxide (NO) in the gaseous phase;

C. liquid-gas interface means having an effluent delivery means extending into said chamber means for conveying and discharging liquid chromatograph effluent thereinto and carrier gas delivery means for directing carrier gas into said chamber means, said effluent delivery means and said carrier gas delivery means cooperating to atomize liquid effluent into said chamber means, both said delivery means cooperating to promote transfer of heat from said chamber means to said liquid effluent and said carrier gas prior to said atomization, said interface means and said chamber means cooperating to vaporize column effluent as a continuous process for preserving the timewise separation of N-nitroso compounds therein;

D. means for establishing a sub-atmospheric pressure in said chamber means for promoting vaporization of said column effluent;

E. means for measuring in the gaseous phase the amount of nitric oxide (NO) liberated in said chamber means; and F. a cold trap interposed between said chamber means and said measuring means for removing chromatograph solvent from the input to said measuring means, said cold trap including an input port for receiving a cold trap input gas from said chamber means and an output port for injecting gaseous cold trap effluent into said measuring means.

2. The apparatus of claim 1, wherein said chamber means comprises a cylindrical chamber, said effluent delivery means comprises a first elongated tube extending into said cylindrical chamber and said carrier gas delivery means comprises a second elongated tube within said chamber surrounding and concentric with said first tube; said first and second tubes extending approximately equal distances into said chamber means to an extent effective to permit heating of said effluent and said carrier gas to a predetermined temperature prior to discharge.

3. The apparatus of claim 2, wherein said interface means further comprises:
a first housing means mounting one end of said first elongated tube;
fluid receiving means for supplying liquid effluent to said one end of said first elongated tube;
a second housing means mounting one end of said second elongated tube and forming with said first housing means a cavity therebetween in fluid communication with said second elongated tube; and
carrier gas receiving means in fluid communication with said cavity.

4. The apparatus of claim 2, wherein said cylindrical chamber is constructed of ceramic material.

5. The apparatus of claim 2, wherein said cylindrical chamber is heated by an electrical heating means external of said cylindrical chamber.

6. The apparatus of claim 5, wherein said electrical heating means is adapted to maintain said cylindrical chamber at a predetermined temperature of at least 300° and not above 500° C.

7. The apparatus of claim 7, wherein the discharge ends of said first and second elongated tubes are positioned in relation to said electrical heating means to operate at a temperature between 100° and 500° C.

* * * * *